US012336783B2

(12) United States Patent
Schulman et al.

(10) Patent No.: US 12,336,783 B2
(45) Date of Patent: Jun. 24, 2025

(54) IDENTIFYING THE VASCULARITY OF CEREBRAL TISSUE IN SUBJECTS USING DEOXYHEMOGLOBIN CONTRAST

(71) Applicant: THORNHILL SCIENTIFIC INC., North York (CA)

(72) Inventors: Jacob B. Schulman, Toronto (CA); Kamil Uludag, Toronto (CA); Joseph Arnold Fisher, Thornhill (CA); David Mikulis, Oakville (CA); Olivia Sobczyk, Etobicoke (CA); Ece Su Sayin, Windsor (CA); Julien Poublanc, Toronto (CA); James Duffin, Toronto (CA)

(73) Assignee: THORNHILL SCIENTIFIC INC., North York (CA)

( * ) Notice: Subject to any disclaimer, the term of this patent is extended or adjusted under 35 U.S.C. 154(b) by 0 days.

(21) Appl. No.: 18/694,505

(22) PCT Filed: Sep. 29, 2022

(86) PCT No.: PCT/IB2022/059311
§ 371 (c)(1),
(2) Date: Mar. 22, 2024

(87) PCT Pub. No.: WO2023/053066
PCT Pub. Date: Apr. 6, 2023

(65) Prior Publication Data
US 2024/0389856 A1    Nov. 28, 2024

Related U.S. Application Data

(60) Provisional application No. 63/249,779, filed on Sep. 29, 2021.

(51) Int. Cl.
*A61B 5/00* (2006.01)
*A61B 5/055* (2006.01)

(52) U.S. Cl.
CPC .......... *A61B 5/0042* (2013.01); *A61B 5/0036* (2018.08); *A61B 5/055* (2013.01);
(Continued)

(58) Field of Classification Search
CPC ..................................... A61B 5/0042
See application file for complete search history.

(56) References Cited

U.S. PATENT DOCUMENTS

2009/0246138 A1    10/2009    Santosh et al.

FOREIGN PATENT DOCUMENTS

CA          3166517 A1      7/2021

OTHER PUBLICATIONS

Fisher, J. et al., "Deoxyhemoglobin Concentration Changes and Cerebral Perfusion Imaging", ClinicTrials.gov, clinical trial Identifier: NCT04537611, Sep. 3, 2020 (Mar. 9, 2020).
(Continued)

*Primary Examiner* — Joseph M Santos Rodriguez
(74) *Attorney, Agent, or Firm* — Perry + Currier Inc.

(57) ABSTRACT

Deoxyhemoglobin contrast has been used to locate arteries based on the earlier blood oxygen-level dependent (BOLD) signal arrival time, higher BOLD signal strength, and shorter mean transit time. However, additional strategies of identifying arteries with oxygen modulation are required to improve the sensitivity and specificity of results. The present disclosure provides a method of distinguishing extravascular voxels from intravascular voxels based on the magnetic signal obtained from two hypoxic boluses having two different baselines. Intravascular voxels are responsive to changes in the baseline due to their high blood volume, while extravascular voxels are not affected by changes to the baseline. Amongst intravascular voxels, arteries can be distinguished from veins because the extraction fraction of
(Continued)

the arterial blood is reduced during hypoxia, and therefore veins are less sensitive to changes in the baseline.

11 Claims, 11 Drawing Sheets

(52) U.S. Cl.
CPC ............ *A61B 5/4884* (2013.01); *A61B 5/489* (2013.01); *A61B 2576/026* (2013.01)

(56) References Cited

OTHER PUBLICATIONS

Sayin, E. S., et al. "Cerebral perfusion imaging: Hypoxia-induced deoxyhemoglobin or gadolinium ?. " bioRxiv (2021).

Poublanc, Julien, et al. "Perfusion MRI using endogenous deoxyhemoglobin as a contrast agent: Preliminary data." bioRxiv preprint doi:: https://doi.org/10.1101/2020.08.21.255802, (2020): 1-22.

Vu, Chau, et al. "Quantitative perfusion mapping with induced transient hypoxia using BOLD MRI." Magnetic resonance in medicine 85.1 (2021): 168-181.

Barajas, R. F., et al. "Distinguishing extravascular from intravascular ferumoxytol pools within the brain: proof of concept in patients with treated glioblastoma." American Journal of Neuroradiology 41.7 (2020): 1193-1200.

Fierstra, J. et al. "Measuring cerebrovascular reactivity: what stimulus to use ?. " The Journal of physiology 591.23 (2013): 5809-5821.

Petrella, Jeffrey R. et al. "MR perfusion imaging of the brain: techniques and applications." American Journal of roentgenology 175.1 (2000): 207-219.

Ogawa, Seiji, et al. "Brain magnetic resonance imaging with contrast dependent on blood oxygenation." proceedings of the National Academy of Sciences 87.24 (1990): 9868-9872.

PCT/IB2022/059311, Identifying the Vascularity of Cerebral Tissue in Subjects Using Deoxyhemoglobin Contrast, Sep. 29, 2022.

IDENTIFYING THE VASCULARITY OF CEREBRAL TISSUE IN SUBJECTS USING DEOXYHEMOGLOBIN CONTRAST

CROSS-REFERENCE TO RELATED APPLICATION(S)

This application claims the benefit of U.S. provisional application entitled "Using Oxygen Modulation in Deoxyhemoglobin Contrast to Highlight Cerebral Arterial and/or Venous Regions" having Ser. No. 63/249,779, filed Sep. 29, 2021 and incorporated by reference herein.

FIELD

The present specification is directed to perfusion magnetic resonance imaging (MRI), and specifically dynamic susceptibility contrast MRI with deoxyhemoglobin as the contrast agent.

BACKGROUND

The present specification is directed to Deoxyhemoglobin, an endogenous substance, is a paramagnetic agent capable of disturbing the magnetic field in and around the blood vessels. Through tightly modulating the oxygenation of blood and preserving isocapnic conditions, using the RespirAct™ RA-MR (Thornhill Medical™, Toronto, Canada), the contrast of deoxyhemoglobin can be modulated in the form of a bolus, which behaves similarly to intravenously injected gadolinium. Thus, deoxyhemoglobin has the potential to be used in perfusion magnetic resonance imaging (MRI) as dynamic susceptibility contrast (DSC).

Deoxyhemoglobin contrast has been used to locate arteries based on the earlier blood oxygen level dependent (BOLD) signal arrival time, higher BOLD signal strength, and shorter mean transit time. However, additional strategies of identifying arteries with oxygen modulation are required to improve the sensitivity and specificity of results.

SUMMARY

An aspect of the specification provides a method of identifying the vascularity of cerebral tissue in a subject using deoxyhemoglobin as a contrast agent. A sequential gas delivery device is used to implement two hypoxic boluses. Each hypoxic bolus can be described as a drop in the partial pressure of oxygen in arterial blood ($\Delta P_aO_2$) in the subject. The first bolus has a higher baseline than the second bolus, but the $\Delta P_aO_2$ in the first and second boluses can be approximately the same.

While inducing the hypoxic boluses, a magnetic resonance imaging system is used to measure the magnetic signal and determine the change in magnetic signal ($\Delta SI$) that results from each the first and second hypoxic boluses. The first and second changes in magnetic signal are compared, and based on the comparison, the voxel is characterized as either A predominantly extravascular voxel or a predominantly intravascular voxel. The voxel may be further characterized as predominantly arterial, predominantly venous or predominantly extravascular tissue.

An aspect of the specification provides a method of identifying the vascularity of cerebral tissue in a subject. A sequential gas delivery (SGD) device is used to implement repeated hypoxic boluses from at least 2 different baseline $P_aO_2$.

First, the SGD device induces a first change in partial pressure of oxygen in arterial blood ($\Delta P_aO_2$) in the subject by targeting a first baseline $P_aO_2$ in the subject and subsequently targeting a first signal $P_aO_2$ in the subject. The first signal $P_aO_2$ is lower than the first baseline $P_aO_2$. While inducing the first change in $P_aO_2$, a magnetic resonance imaging (MRI) device determines a first change in magnetic signal ($\Delta SI$) in a voxel of the subject's brain.

Next, the SGD device induces a second $\Delta P_aO_2$ in the subject using the sequential gas delivery device by targeting a second baseline $P_aO_2$ in the subject and subsequently targeting a second signal $P_aO_2$ in the subject. The second signal $P_aO_2$ is lower than the second baseline $P_aO_2$ and the second baseline $P_aO_2$ is lower than the first baseline $P_aO_2$. While inducing the second $\Delta P_aO_2$, the MRI device determines a second $\Delta SI$ in a voxel of the subject's brain.

Next, the MRI device compares the first and second $\Delta SI$ and, based on the comparison, outputs a signal at a user interface connected to the MRI device, the signal indicating whether the voxel is extravascular or intravascular. In specific examples, the signal indicates whether the voxel is predominantly arterial, predominantly venous or predominantly extravascular tissue.

In some examples, the first $\Delta P_aO_2$ is approximately equal to the second $\Delta P_aO_2$.

In further examples, comparing the first $\Delta SI$ and second $\Delta SI$ comprises calculating a difference between the first $\Delta SI$ and second $\Delta SI$. The method includes the additional steps of outputting a signal at the user interface indicating that the voxel is extravascular if the first $\Delta SI$ is approximately equal to the second change in magnetic signal $\Delta SI$, and outputting a signal at the user interface indicating that the voxel is intravascular if the second $\Delta SI$ is higher than the first $\Delta SI$.

In yet further examples, comparing the first $\Delta SI$ and second $\Delta SI$ comprises dividing the second $\Delta SI$ by the first $\Delta SI$ to obtain a dividend. The method includes the additional steps of outputting a signal at the user interface indicating that the voxel is extravascular if the dividend is approximately 1, and outputting a signal at the user interface indicating that the voxel is intravascular if the dividend is greater than approximately 1.

In some examples, the method includes the additional step of comparing the dividend to a pre-determined threshold. If the dividend is less than or equal to the pre-determined threshold, the user interface outputs a signal indicating that the voxel contains a vein. If the dividend is greater than the pre-determined threshold, the user interface outputs a signal indicating that the voxel contains an artery.

In further examples, the method includes the additional step of maintaining normocapnia while inducing the first and second $\Delta P_aO_2$.

In yet further examples, the first baseline $P_aO_2$ is between 85 and 100 mmHg.

In some examples, the second baseline $P_aO_2$ is between 75 and 85 mmHg.

Another aspect of the specification provides a non-transitory machine-readable medium comprising instructions that, when executed by a processor, cause the processor to perform the above-described method.

A further aspect of the specification provides an apparatus for identifying the vascularity of cerebral tissue in a subject. The apparatus includes a sequential gas delivery (SGD) device for controlling the partial pressure of oxygen in arterial blood in the subject. The SGD device may further control the partial pressure of arterial carbon dioxide in the subject.

Connected to the sequential gas delivery device is a processor which is configured to control the SGD device to induce a first and second change in partial pressure of oxygen in arterial blood ($\Delta P_aO_2$) in the subject. To induce the first $\Delta P_aO_2$, the processor controls the SGD device to target a first baseline partial pressure of oxygen in arterial blood ($P_aO_2$) in the subject and subsequently target a first signal partial pressure of oxygen in arterial blood ($P_aO_2$) in the subject. The first signal $P_aO_2$ is lower than the first baseline $P_aO_2$. To induce the second $\Delta P_aO_2$, the processor controls the SGD device to target a second baseline partial pressure of oxygen in arterial blood ($P_aO_2$) in the subject and subsequently target a second signal partial pressure of oxygen in arterial blood ($P_aO_2$) in the subject. The second signal $P_aO_2$ is lower than the second baseline $P_aO_2$. The second baseline $P_aO_2$ is lower than the first baseline $P_aO_2$.

Connected to the processor is a sensor. The sensor is configured to determine a first change in magnetic signal ($\Delta SI$) in a voxel of the subject's brain while the sequential gas delivery device induces the first $\Delta P_aO_2$ and determine a second change in magnetic signal ($\Delta SI$) in the voxel of the subject's brain while the sequential gas delivery device induces the second $\Delta P_aO_2$.

The processor is further configured to receive the first and second $\Delta SI$ from the sensor and compare the two values. A user interface connected to the processor is configured to output a signal indicating whether the voxel is extravascular or intravascular based on the comparison.

In some examples, the user interface may be configured to output a signal whether the voxel is predominantly venous or arterial based on the comparison.

In some examples, the first $\Delta P_aO_2$ is approximately equal to the second $\Delta P_aO_2$.

These together with other aspects and advantages which will be subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

Embodiments are described with reference to the following figures.

DETAILED DESCRIPTION

Figure 1:
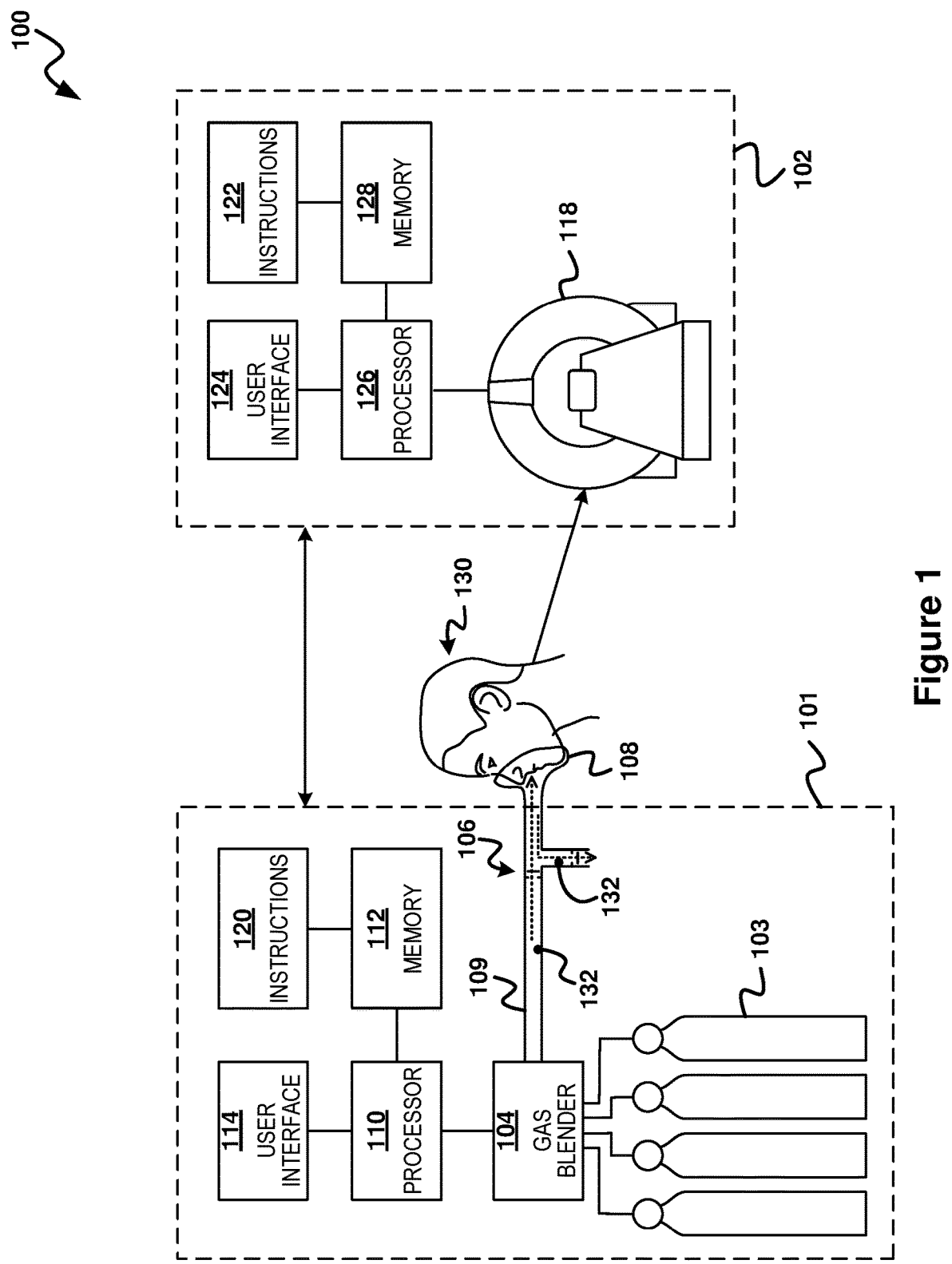
FIG. 1 is a block diagram of a system for identifying cerebral vessels and tissue using deoxyhemoglobin as a contrast agent.

Table 1 provides the definitions of abbreviations used herein.

| Abbreviation | Definition |
| --- | --- |
| $\Delta SI$ | change in signal, particularly a change in BOLD signal |
| $SI_{baseline}$ | baseline magnetic signal, particularly a baseline BOLD signal |
| $SI_{peak}$ | peak magnetic signal, particularly a peak BOLD signal |
| $\Delta R^*_{2,max}$ | change in relaxation rate |
| AFNI | Analysis of Functional Neuroimages |
| AIF | arterial input function |
| ASIC | application-specific integrated circuit |
| ASL | arterial spin labelling |
| BOLD | Blood Oxygen Level Dependent |
| CBF | cerebral blood flow |
| CBV | cerebral blood volume |
| $CMRO_2$ | metabolic rate of oxygen |
| CPU | central processing unit |
| [dOHb] | Concentration of deoxyhemoglobin |
| DSC | Dynamic susceptibility contrast |
| EEPROM | electrically erasable programmable read-only memory |
| FPGA | field-programmable gate array |
| FRC | functional residual capacity |
| G1 | first gas |
| G2 | second gas |
| HB | high baseline |
| LB | low baseline |
| MRI | magnetic resonance imaging |
| MTT | mean transit time |
| OEF | oxygen extraction fraction |
| $P_aCO_2$ | arterial partial pressure of carbon dioxide |
| $P_aO_2$ | arterial partial pressure of oxygen |
| $PCO_2$ | partial pressure of carbon dioxide |
| $PO_2$ | partial pressure of oxygen |
| PET | positron emission tomography |
| $P_{ET}CO_2$ | end tidal partial pressure of carbon dioxide |
| $P_{ET}O_2$ | end tidal partial pressure of oxygen |
| RAM | random access memory |
| $\Delta R^*_{2,max}$ | Maximum relaxation rate |
| ROI | region of interest |
| ROM | read-only memory |
| SGD | sequential gas delivery |
| $S_aO_2$ | arterial blood-oxygen saturation |
| TE | echo time |
| TR | repetition time |
| VT | tidal volume |

"Vessel" or "blood vessel" herein refers to a vein, artery, or capillary.

"Extravascular" herein refers to components or events occurring outside the vascular system.

"Intravascular" herein refers to components or event occurring within the vascular system.

"Normocapnia" herein refers to a state of normal arterial carbon dioxide pressure in a subject, usually about 40 mmHg.

"Normoxia" herein refers to a state of normal oxygen pressure in a subject, usually about 80 to 100 mmHg.

"Hypoxia" herein refers to a state of depressed oxygen pressure in a subject's vascular system, usually below 80 mmHg.

"Hyperoxia" herein refers to a state of elevated oxygen pressure in a subject's vascular system, usually above 100 mmHg.

The present disclosure provides a system and method for identifying the vascularity of cerebral tissue using deoxyhemoglobin as a contrast agent. By inducing a deoxyhemoglobin bolus and measuring the resulting BOLD signal in a voxel, large blood vessels can be identified. A deoxyhemoglobin bolus produces a stronger BOLD signal in a vein or artery when the baseline $P_aO_2$ is lower, even if the change in [dOHb] is the same. This is because the oxyhemoglobin dissociation curve is steeper when the $PO_2$ is lower. In contrast, voxels that contain mostly extravascular tissues will not be influenced by the baseline $PO_2$ due to the lower blood volume (CBV).

FIG. 1 shows a system 100 for identifying the vascularity of cerebral tissue using deoxyhemoglobin as a contrast agent. The system 100 includes a sequential gas delivery (SGD) device 101 to provide delivery gases to a subject 130 and target a $P_aO_2$. Using the SGD device, targeted $P_aO_2$ values may be attained while maintaining normocapnia. The system 100 further includes a magnetic resonance imaging (MRI) device 102. The SGD device 101 includes gas supplies 103, a gas blender 104, a mask 108, a processor 110, memory 112, and a user interface 114. The SGD device 101 may be configured to control end-tidal partial pressure of $CO_2$ ($P_{ET}CO_2$) and end-tidal partial pressure of $O_2$ ($P_{ET}O_2$) by generating predictions of gas flows to actuate target end-tidal values. The SGD device 101 may be an RespirAct™ device (Thornhill Medical™: Toronto, Canada) specifically configured to implement the techniques discussed herein. For further information regarding sequential gas delivery, U.S. Pat. No. 8,844,528, US Publication No. 2018/0043117, and U.S. Pat. No. 10,850,052, which are incorporated herein by reference, may be consulted.

The gas supplies 103 may provide carbon dioxide, oxygen, nitrogen, and air, for example, at controllable rates, as defined by the processor 110. A non-limiting example of the gas mixtures provided in the gas supplies 103 is:

a. Gas A: 10% $O_2$, 90% $N_2$;
b. Gas B: 10% $O_2$, 90% $CO_2$;
c. Gas C: 100% $O_2$; and
d. Calibration gas: 10% $O_2$, 9% $CO_2$, 81% $N_2$.

The gas blender 104 is connected to the gas supplies 103, receives gases from the gas supplies 103, and blends received gases as controlled by the processor 110 to obtain a gas mixture, such as a first gas (G1) and a second gas (G2) for sequential gas delivery.

The second gas (G2) is a neutral gas in the sense that it has about the same $PCO_2$ as the gas exhaled by the subject 130, which includes about 4% to 5% carbon dioxide. In some examples, the second gas (G2) may include gas actually exhaled by the subject 130. The first gas (G1) has a composition of oxygen that is equal to the target $P_{ET}O_2$ and preferably no significant amount of carbon dioxide. For example, the first gas (G1) may be air (which typically has about 0.04% carbon dioxide), may consist of 21% oxygen and 79% nitrogen, or may be a gas of similar composition, preferably without any appreciable $CO_2$.

The processor 110 may control the gas blender 104, such as by electronic valves, to deliver the gas mixture in a controlled manner.

The mask 108 is connected to the gas blender 104 and delivers gas to the subject 130. The mask 108 may be sealed to the subject's face to ensure that the subject only inhales gas provided by the gas blender 104 to the mask 108. In some examples, the mask is sealed to the subject's face with skin tape such as Tegaderm™ (3M™: Saint Paul, Minnesota). A valve arrangement 106 may be provided to the SGD device 101 to limit the subject's inhalation to gas provided by the gas blender 104 and limit exhalation to the room. In the example shown, the valve arrangement 106 includes an inspiratory one-way valve from the gas blender 104 to the mask 108, a branch between the inspiratory one-way valve and the mask 108, and an expiratory one-way valve at the branch. Hence, the subject 130 inhales gas from the gas blender 104 and exhales gas to the room.

The subject 130 may breathe spontaneously or be mechanically ventilated.

The gas supplies 103, gas blender 104, and mask 108 may be physically connectable by a conduit 109, such as tubing, to convey gas. Any suitable number of sensors 132 may be positioned at the gas blender 104, mask 108, and/or conduits 109 to sense gas flow rate, pressure, temperature, and/or similar properties and provide this information to the processor 110. Gas properties may be sensed at any suitable location, so as to measure the properties of gas inhaled and/or exhaled by the subject 130.

The processor 110 may include a central processing unit (CPU), a microcontroller, a microprocessor, a processing core, a field-programmable gate array (FPGA), an application-specific integrated circuit ($\Delta$SIC), or a similar device capable of executing instructions. The processor 110 may be connected to and cooperate with the memory 112 that stores instructions and data.

The memory 112 includes a non-transitory machine-readable medium, such as an electronic, magnetic, optical, or other physical storage device that encodes the instructions. The medium may include, for example, random access memory (RAM), read-only memory (ROM), electrically erasable programmable read-only memory (EEPROM), flash memory, a storage drive, an optical device, or similar.

The user interface 114 may include a display device, touchscreen, keyboard, speaker, microphone, indicator, buttons, the like, or a combination thereof to allow for operator input and/or output.

Instructions 120 may be provided to carry out the functionality and methods described herein. The instructions 120 may be directly executed, such as a binary file, and/or may include interpretable code, bytecode, source code, or similar instructions that may undergo additional processing to be executed. The instructions 120 may be stored in the memory 112.

System 100 further includes an MRI device 102 for conducting magnetic resonance imaging on the subject 130. A suitable MRI system may include a sensor 118 such as a 3T MRI system. A suitable example of a 3T MRI system is the Signa HDxt 3.0T™, provided by GE Healthcare (Milwaukee, USA). In addition to the sensor 118, the MRI device 102 may further include a processor 126, a memory 128, and a user interface 124. Any description of the processor 126 may apply to the processor 110 and vice versa. Likewise, any description of memory 128 may apply to memory 112 and vice versa. Similarly, any description of instructions 122 may apply to instructions 120 and vice versa. Also, any description of user interface 124 may apply to user interface 114, and vice versa. In some implementations, the MRI device 102 and the SGD device 101 share one or more of a memory, processer, user interface, and instructions, however, in the present disclosure, the MRI device 102 and the SGD device 101 will be described as having respective processors, user interfaces, memories, and instructions. The processor 110 of the SGD device 101 may transmit data and instructions to the processor 126 of the MRI device 102. The processor 126 of the MRI device 102 may transmit data and instructions to the processor 110 of the SGD device 101. The system 100 may be configured to synchronize MRI imaging obtained by the MRI device 102 with measurements obtained by the SGD device 101.

The processor 126 may retrieve operating instructions 122 from the memory 128 or from the user interface 124. The operating instructions 122 may include image acquisition parameters. The parameters may include an interleaved echo-planar acquisition consisting of a number of contiguous slices, a defined isotropic resolution, a diameter for the field of view, a repetition time (TR), and an echo time. In one implementation, the number of contiguous slices is 27, the isotropic resolution is 3 mm, the field of view is 19.6 cm, the echo time is 30 ms, and the TR is 2000 ms, however a range of values will be apparent to a person of ordinary skill in the art. The operating instructions 122 may also include parameters for a high-resolution T1-weighted SPGR (Spoiled Gradient Recalled) sequence for co-registering the BOLD images and localizing the arterial and venous components. The SPGR parameters may include a number of slices, a dimension for the partitions, an in-plane voxel size, a diameter for the field of view, an echo time, and a repetition time. In one implementation, the number of slices is 176 m, the partitions are 1 mm thick, the in-plane voxel size is 0.85 by 0.85 mm, the field of view is 22 cm, the echo time is 3.06 ms, and the TR is 7.88 ms.

The processor 126 may be configured to analyze the images using image analysis software such as Matlab 2015a and AFNI (Analysis of Functional Neuroimages: US National Institutes of Health) or other processes generally known in the art. As part of the analysis, the processor 126 may be configured to perform slice time correction for alignment to the same temporal origin and volume spatial re-registration to correct for head motion during acquisition. The processor 126 may be further configured to perform standard polynomial detrending. In one implementation, the processor 126 is configured to detrend using AFNI software 3dDeconvolve to obtain detrended data.

The user interface 124 may include a display device, touchscreen, keyboard, speaker, indicator, microphone, buttons, the like, or a combination thereof to allow for operator input and/or output. Data generated and images acquired by the processor 126 may be displayed at the user interface 124.

Figure 2:
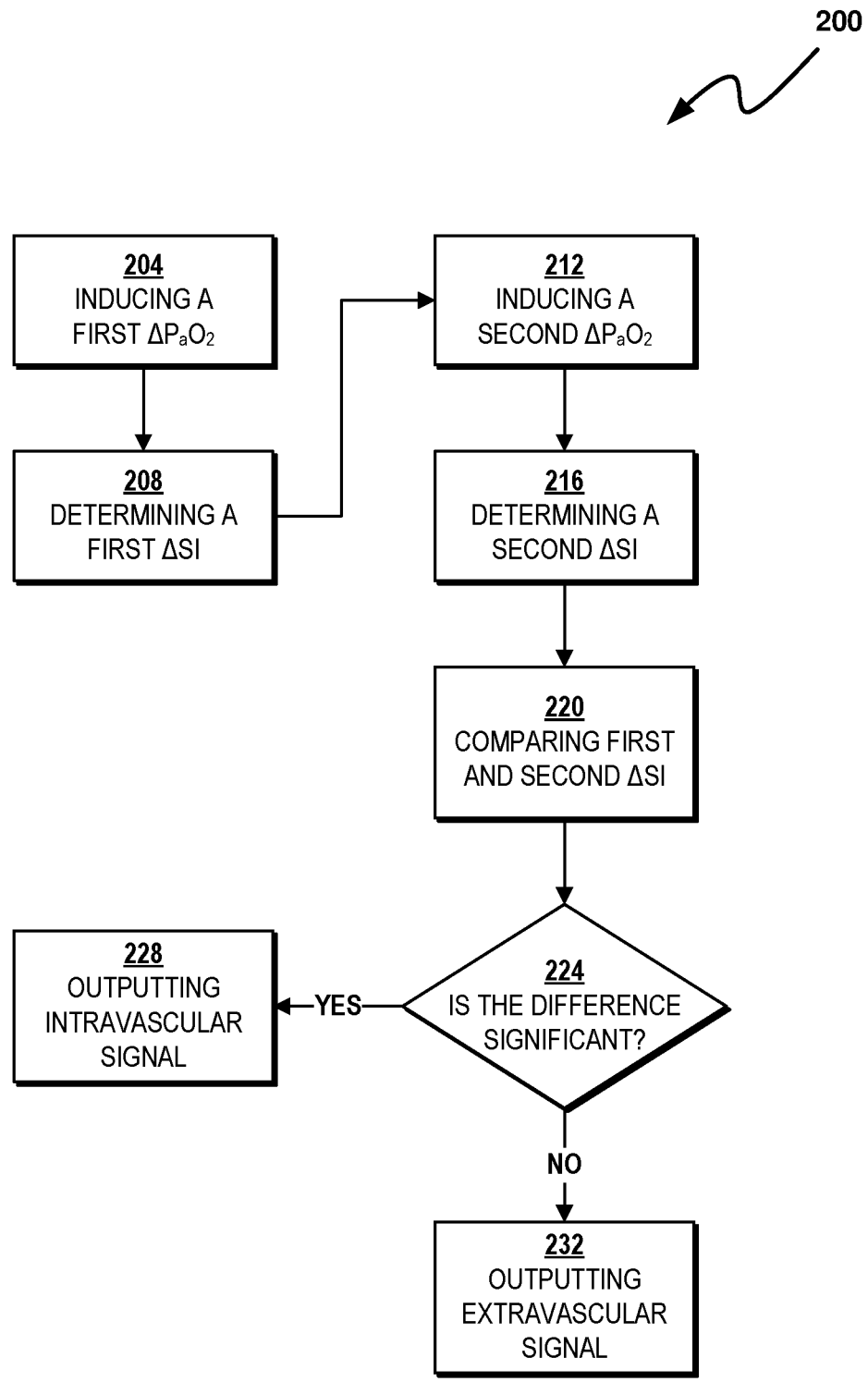
FIG. 2 is a flowchart of a method for identifying cerebral vessels and tissue using deoxyhemoglobin as a contrast agent.

FIG. 2 shows an example method 200 of identifying the vascularity of cerebral tissue in a subject. The method 200 may be performed using the system 100.

At block 204, the SGD device 101 induces a first change in partial pressure of oxygen in arterial blood ($\Delta P_aO_2$) in the subject 130. Block 204 may be performed in response to instructions 120 executed at the processor 110. As part of block 204, the SGD device 101 establishes a first baseline $P_aO_2$ in the subject 130 and subsequently targets a first signal $P_aO_2$ in the subject 130. The SGD device 101 may target the $P_aO_2$ value long enough for the sensor 118 to obtain a stable measurement. The length of time may depend on the signal-to-noise ratio (SNR), and the duration may be reduced if the SNR can be reduced. In some examples, 15 seconds is adequate. In further examples, 30 seconds is adequate. In other examples, the SGD device 101 may target the $PO_2$ for at least five TR once the targeted $P_aO_2$ value is reached.

The first baseline $P_aO_2$ may be at or near normoxia. In particular examples, the first baseline $P_aO_2$ is approximately 85 to 100 mmHg. The first signal $P_aO_2$ is lower than the first baseline and may be selected to induce hypoxia in the subject 130. In particular examples, the first signal $P_aO_2$ is approximately 40 mmHg below the first baseline $P_aO_2$. In further examples, the first signal $P_aO_2$ is approximately 30 mmHg below the first baseline $P_aO_2$. In yet further examples, the first signal $P_aO_2$ and the first baseline $P_aO_2$ are selected such that the [dOHb] at the first signal $P_aO_2$ is 25% lower than the [dOHb] at the first baseline $P_aO_2$. The first baseline and first signal $P_aO_2$ are selected to induce a measurable [dOHb] signal in the subject 130. By targeting the baseline $P_aO_2$ followed by the signal $P_aO_2$, a hypoxic bolus is generated in the subject's pulmonary arteries which passes into the subject's brain. After targeting the first signal $P_aO_2$, the SGD device 101 may again target the first baseline $P_aO_2$ or return to normoxia, such that the bolus is transient. Targeting the signal $P_aO_2$ for brief amounts of time and returning to baseline or normoxia $P_aO_2$ may produce adequate signals while reducing subject discomfort associated with hypoxia.

While the SGD device 101 is performing block 204, the MRI device 102 determines the resulting change to a magnetic signal in the voxel. The MRI device 102 may perform this step in response to instructions 122 executed at processor 126 and received from the memory 128. The processor 126 may control the sensor 118 to measure a magnetic signal continuously or at discrete intervals while the SGD device 101 is inducing the first $\Delta P_aO_2$. Because oxyhemoglobin is diamagnetic while deoxyhemoglobin is paramagnetic, the hypoxic bolus distorts the magnetic field of the MRI device 102. In one example, the sensor 118 measures a T2* dependent signal, also called the Blood Oxygen-Level Dependent (BOLD) signal. To determine the change in magnetic signal, the sensor 118 measures a first magnetic signal in the voxel while the SGD device 101 is targeting the first baseline $P_aO_2$ and subsequently the sensor 118 measures a second magnetic signal in the voxel while the SGD device 101 is targeting the first signal $P_aO_2$. To ensure that the measurements correspond with the targeted $P_aO_2$, the sensor 118 may measure the magnetic signal only after the processor 110 determines that the respective targeted $P_aO_2$ has been reached. In some examples, the sensor 118 measures the minimum signal detected when targeting the baseline $P_aO_2$ and then measures the maximum magnetic signal detected when targeting the signal $P_aO_2$. The measured magnetic signals may be stored in the memory 128.

At block 208, the MRI device 102 determines a first change in the magnetic signal ($\Delta SI$). Block 208 is performed by the processor 126 in response to instructions 122 received from the memory 128. The processor 126 may compute the first $\Delta SI$ based on a comparison between the first and second magnetic signals measured at block 204. In some examples, the first $\Delta SI$ is calculated by subtracting the magnetic signal measured at the first baseline $P_aO_2$ from the magnetic signal measured at the first signal $P_aO_2$. In some examples, the first $\Delta SI$ is calculated according to Equation 1, where $SI_{baseline}$ represents the magnetic signal measured at the first baseline $P_aO_2$ and $SI_{peak}$ represents the magnetic signal measured at the first signal $P_aO_2$. The first $\Delta BOLD$ may be stored in the memory 128.

$$\Delta SI(\%) = \frac{(SI_{baseline} - SI_{peak})}{SI_{baseline}} * 100 \qquad \text{Equation 1}$$

At block 212, the SGD device 101 induces a second change in partial pressure of oxygen in arterial blood ($\Delta P_aO_2$) in the subject 130. Block 212 may be performed in response to instructions 120 executed at the processor 110. As part of block 212, the SGD device 101 establishes a second baseline $P_aO_2$ in the subject 130 and subsequently targets a second signal $P_aO_2$ in the subject 130. The SGD device 101 may target the $P_aO_2$ value long enough for the sensor 118 to obtain a stable measurement. The length of time may depend on the signal-to-noise ratio (SNR), and the duration may be reduced if the SNR can be reduced. In some examples, 15 seconds is adequate. In further examples, 30 seconds is adequate. In other examples, the SGD device 101 may target the $PO_2$ for at least five TR once the targeted $P_aO_2$ value is reached.

The second baseline $P_aO_2$ may be at or near normoxia, but the second baseline $P_aO_2$ is lower than the first baseline $P_aO_2$. In particular examples, the second baseline $P_aO_2$ is approximately 75 to 85 mmHg. The second signal $P_aO_2$ is lower than the second baseline $P_aO_2$ and may be selected to induce hypoxia in the subject 130.

Figure 3:
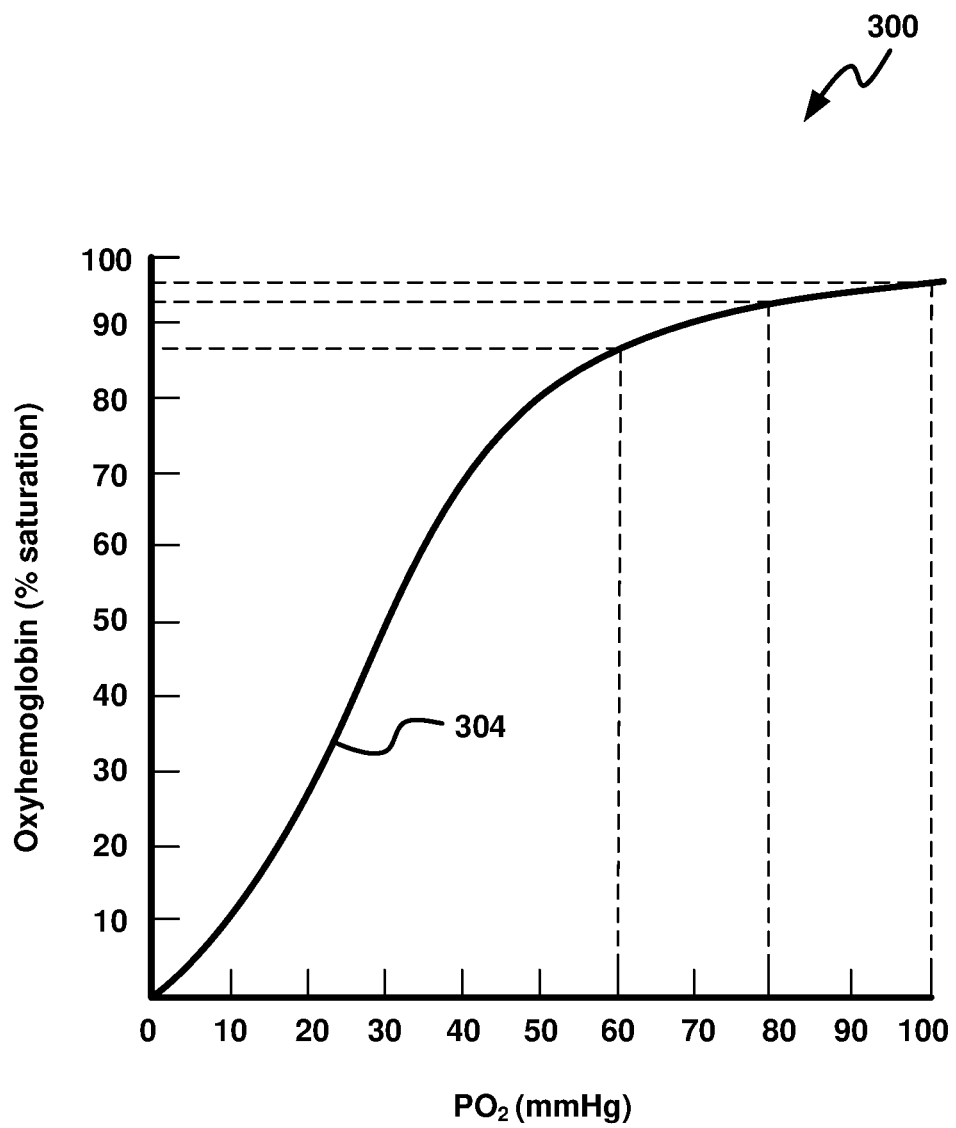
FIG. 3 is a graph of an oxygen-hemoglobin dissociation curve.

As part of blocks 204 and 212, the processor 126 may select the first and second baseline $P_aO_2$ based on the oxygen-hemoglobin dissociation curve. An example of an oxygen-hemoglobin dissociation curve 304 is shown in FIG. 3. FIG. 3 shows a graph 300 with the oxyhemoglobin (measured in % saturation) plotted on the y-axis and $PO_2$ (measured in mmHg) plotted on the x-axis. The processor 126 may select the first baseline $P_aO_2$ from the upper, flattened portion of the oxygen-hemoglobin dissociation curve 304 while the processor 126 may select the second baseline $P_aO_2$ to be on a steeper portion of the oxygen-hemoglobin dissociation curve 304.

In particular examples, the second signal $P_aO_2$ is approximately 40 mmHg below the second baseline $P_aO_2$. In further examples, the second signal $P_aO_2$ is approximately 30 mmHg below the second baseline $P_aO_2$. In yet further examples, the second signal $P_aO_2$ and the second baseline $P_aO_2$ are selected such that the [dOHb] at the second signal $P_aO_2$ is 25% lower than the [dOHb] at the second baseline $P_aO_2$. The second baseline and second signal $P_aO_2$ are selected to induce a measurable [dOHb] signal in the subject 130. By targeting the baseline $P_aO_2$ followed by the signal $P_aO_2$, a hypoxic bolus is generated in the subject's pulmonary arteries which passes into the subject's brain. After targeting the second signal $P_aO_2$, the SGD device 101 may again target the second baseline $P_aO_2$ or return to normoxia, such that the bolus is transient. Targeting the signal $P_aO_2$ for brief amounts of time and returning to baseline or normoxia $P_aO_2$ may produce adequate signals while reducing subject discomfort associated with hypoxia.

While the SGD device 101 is performing block 212, the MRI device 102 determines the resulting change to a magnetic signal in the voxel. The MRI device 102 may perform this step in response to instructions 122 executed at processor 126 and received from the memory 128. The processor 126 may control the sensor 118 to measure a magnetic signal continuously or at discrete intervals while the SGD device 101 is inducing the first $\Delta P_aO_2$. Because oxyhemoglobin is diamagnetic while deoxyhemoglobin is paramagnetic, the hypoxic bolus distorted the magnetic field of the sensor 118. In one example, the sensor 118 measures a T2* dependent signal, also called the Blood Oxygen-Level Dependent (BOLD) signal. To determine the change in magnetic signal, the sensor 118 measures a third magnetic signal in the voxel while the SGD device 101 is targeting the second baseline $P_aO_2$ and subsequently the sensor 118 measures a fourth magnetic signal in the voxel while the SGD device 101 is targeting the second signal $P_aO_2$. To ensure that the measurements correspond with the targeted $P_aO_2$, the sensor 118 may measure the magnetic signal only after the processor 10 determines that the respective targeted $P_aO_2$ has been reached. In some examples, the sensor 118 measures the minimum signal detected when targeting the baseline $P_aO_2$ and then measures the maximum magnetic signal detected when targeting the signal $P_aO_2$. The measured magnetic signals may be stored in the memory 128.

At block 216, the MRI device 102 determines a second change in the magnetic signal ($\Delta SI$). Block 208 is performed by the processor 126 in response to instructions 122 received from the memory 128. The processor 126 may compute the second $\Delta SI$ based on a comparison between the third and fourth magnetic signals measured at block 212. In some examples, the second $\Delta SI$ is calculated by subtracting the magnetic signal measured at the second baseline $P_aO_2$ from the magnetic signal measured at the second signal $P_aO_2$. In some examples, the first $\Delta SI$ is calculated according to Equation 1, where $SI_{baseline}$ represents the magnetic signal measured at the second baseline $P_aO_2$ and $SI_{peak}$ represents the magnetic signal measured at the second signal $P_aO_2$. The second $\Delta SI$ may be stored in the memory 128.

In FIG. 2, the SGD device 101 targets the first baseline $P_aO_2$ before targeting the second baseline $P_aO_2$, however the method 200 is not particularly limited. Block 212 may be performed before block 204. In other words, the SGD device 101 may target the lower baseline $P_aO_2$ and then target the higher baseline $P_aO_2$.

In FIG. 2, the SGD device 101 induces a first change in $P_aO_2$ and determines the first $\Delta SI$ before inducing a second change in $P_aO_2$ and determining the second $\Delta SI$, however the method 200 is not particularly limited. Block 212 may be performed before block 208. In other words, the SGD device 101 may inducing the first and second change in $P_aO_2$ before determining the first and second $\Delta SI$.

At block 220, the processor 126 compares the first $\Delta SI$ to the second $\Delta SI$. In some examples, the comparison at block 220 comprises subtracting the first $\Delta SI$ from the second $\Delta SI$ to obtain a difference. In other examples, the comparison at block 220 comprises dividing the first $\Delta SI$ by the second $\Delta SI$ to obtain a dividend. The remaining steps in method 200 will be described with reference to examples where the first $\Delta SI$ is subtracted from the second $\Delta SI$ to obtain a difference.

To ensure that the first and second $\Delta SI$ are comparable, the difference between the first baseline $P_aO_2$ and the first signal $P_aO_2$ is approximately the same as the difference between the second baseline $P_aO_2$ and the second signal $P_aO_2$. In a non-limiting example, the first baseline $P_aO_2$ is 90 mmHg, the first signal $P_aO_2$ is 60 mmHg, the second baseline $P_aO_2$ is 80 mmHg, and the second signal $P_aO_2$ is 50 mmHg. In this example, both the first and second hypoxic boluses implement a drop of 30 mmHg. Because the BOLD signal is subject to considerable noise and drift, the difference between the baseline and signal $P_aO_2$ should be selected to provide a clear signal. In some examples, a 25% change in [dOHb] is sufficient to provide a clear signal, however smaller changes in [dOHb] may be effective if the signal-to-noise ratio (SNR) can be improved.

At block 224, the processor 126 determines whether or not the difference between the first $\Delta SI$ and the second $\Delta SI$ is significant. As part of block 224, the processor 126 may compare the difference to a pre-determined threshold. If the second $\Delta SI$ is significantly larger than the first $\Delta SI$, the processor 126 characterizes the voxel as intravascular. The characterization indicates that the voxel predominantly contains intravascular components such as blood, or that the voxel contains a large blood vessel. If the second $\Delta SI$ is close to or approximately the same as the first $\Delta SI$, the processor 126 characterizes the voxel as extravascular. The characterization indicates that the voxel predominantly contains extravascular components such as cerebral tissues, or that the voxel does not contain any large blood vessels.

In some examples, block 220 further includes determining whether the first ΔSI is greater than the second ΔSI. Regardless of the difference calculated at block 224, if the first ΔSI is greater than the second ΔSI, the processor 126 may nonetheless characterize the voxel as extravascular. In some examples, if the processor 126 determines that the first ΔSI is greater than the second ΔSI, the processor 126 may skip block 224 and proceed directly to block 232.

The reasoning behind this determination can be best understood with reference to the oxygen-hemoglobin dissociation curve, an example of which is shown in FIG. 3. Under normal physiologic conditions, the oxygen-hemoglobin dissociation curve 304 is fairly flat when $PO_2$ is above 80 mmHg, so a hypoxic bolus generated from a baseline of 100 mmHg will minimally affect the magnetic signal. In contrast, the oxygen-hemoglobin dissociation curve 304 is steeper below 80 mmHg and begins to flatten out again when hemoglobin is about 50% saturated which in healthy people at sea level is about 29 mmHg. Therefore, a hypoxic bolus generated from a baseline of 80 mmHg will affect the magnetic signal to a greater degree than when starting at $PO_2$ above 80 mmHg. This is illustrated by the dotted lines which show that a 20 mmHg decrease in $PO_2$ from 100 mmHg to 80 mmHg only minimally reduces the oxyhemoglobin as compared to a 20 mmHg decrease from 80 mmHg to 60 mmHg.

The sensitivity of a voxel to the baseline $P_aO_2$ during implementation of method 200 will depend on the cerebral blood volume of said voxel. A voxel containing a large vessel will be sensitive to a shift in the baseline $P_aO_2$ and therefore the second ΔSI will be significantly greater than the first ΔSI. In contrast, a voxel containing only small vessels will be less sensitive to a shift in the baseline $P_aO_2$ and therefore the second ΔSI will be close to or approximately the same as the first ΔSI.

At block 228, the user interface 124 outputs a signal indicating that the voxel is intravascular. Block 228 is performed by the user interface 124 in response to a determination at block 224 that the second ΔSI is significantly larger than the first ΔSI, As part of block 228, the processor 126 controls the user interface 124 to output a signal indicating that the voxel is predominantly intravascular.

At block 232, the user interface 124 outputs a signal indicating that the voxel is extravascular. Block 232 is performed by the user interface 124 in response to a determination at block 224 that the second ΔSI is close to or approximately the same as the first ΔSI. As part of block 232, the processor 126 controls the user interface 124 to output a signal indicating that the voxel is predominantly extravascular.

The signals generated at blocks 228 and 232 may comprise a light, sound, colour, vibration, chart, image, alert, notification, alarm, verbal message, or the like. The signal at block 228 may be selected to contrast the signal output at block 232. In some implementations, the processor 126 generates an image of the subject's brain, or a portion of the subject's brain which is displayed by the user interface at block 228 or 232. The image includes a region corresponding to voxels which are coloured to indicate whether the voxel is predominantly intravascular artery or intravascular vein, or extravascular. In further examples, the method 200 is performed for a plurality of voxels and the processor 126 generates an image indicating whether each of the plurality of voxels is predominantly intravascular artery or vein, or extravascular.

In examples where the comparison at block 220 comprises dividing the second ΔSI by the first ΔSI to obtain a dividend, the processor 126 compares the dividend to a first pre-determined threshold. If the dividend is less than or equal to the first threshold, the processor 126 characterizes the voxel as extravascular and proceeds to block 232. If the dividend is greater than the first threshold, the processor 126 characterizes the voxel as intravascular and proceeds to block 228. In specific examples, the first threshold is 1 or approximately 1. If the dividend is 1 or close to 1, the second ΔSI is approximately the same as the first ΔSI, indicating that the voxel is predominantly extravascular, for reasons explained above with respect to FIG. 3.

If the processor determines that the voxel is predominantly intravascular, the processor 126 may further compare the dividend to a second pre-determined threshold. If the dividend is less than or equal to the second threshold, the processor 126 determines that the voxel contains a vein. As part of block 232, the processor 126 controls the user interface 124 to output a signal indicating that the voxel contains a vein. If the dividend is greater than the second threshold, the processor 126 determines that the voxel contains an artery. In particular examples, the second threshold is approximately 2. As part of block 232, the processor 126 controls the user interface 124 to output a signal indicating that the voxel contains an artery.

The reasoning behind this determination is that the extraction fraction of the arterial blood is reduced during hypoxia. Therefore, the changes to [dOHb] in the veins is less than the changes to [dOHb] in the arteries. In voxels containing large arteries, the second ΔSI (generated from a low baseline) may be at least 200% larger than the first ΔSI.

It is noted that these relationships do not apply to voxels containing lower blood volumes, as is the case in tissue parenchyma. An arterial or venous voxel afflicted by tissue parenchyma may contain only 20% blood volume as compared to a healthy voxel.

Another way to distinguish voxels containing arteries is by comparing the magnetic signals measured by the sensor 118 while targeting the first and second baseline $P_aO_2$. The magnetic signal measured at baseline will be higher in arteries than in veins or extravascular tissue. In voxels that contain predominantly extravascular tissue, the magnetic signal at both the first and second baseline $P_aO_2$ will be relatively low. Similarly, in voxels that are predominantly venous, the magnetic signal at both the first and second baseline $P_aO_2$ will both be relatively low. In voxels that are predominantly arterial, the magnetic signal at both the first and second baseline $P_aO_2$ will be relatively high. In some examples, the processor 126 will determine the vascularity of the voxel based on both the magnetic signal at baseline and a comparison between the first and second ΔSI.

The method will now be described by way of example. In the following examples, a high baseline $P_aO_2$ corresponds to $S_aO_2=98\%$, a low baseline $P_aO_2$ corresponds to $S_aO_2=88\%$, and a medium baseline $P_aO_2$ corresponds to $S_aO_2=93\%$. A small $\Delta P_aO_2$ corresponds to a baseline $S_aO_2$ of 98% and a signal of 90% or a baseline $S_aO_2$ of 88% and a signal of 80%. A medium $\Delta P_aO_2$ corresponds to a baseline of 98% and a signal of 84%. A high $\Delta P_aO_2$ corresponds to a baseline $S_aO_2$ of 98% and a signal $S_aO_2$ of 75%.

Figure 4:
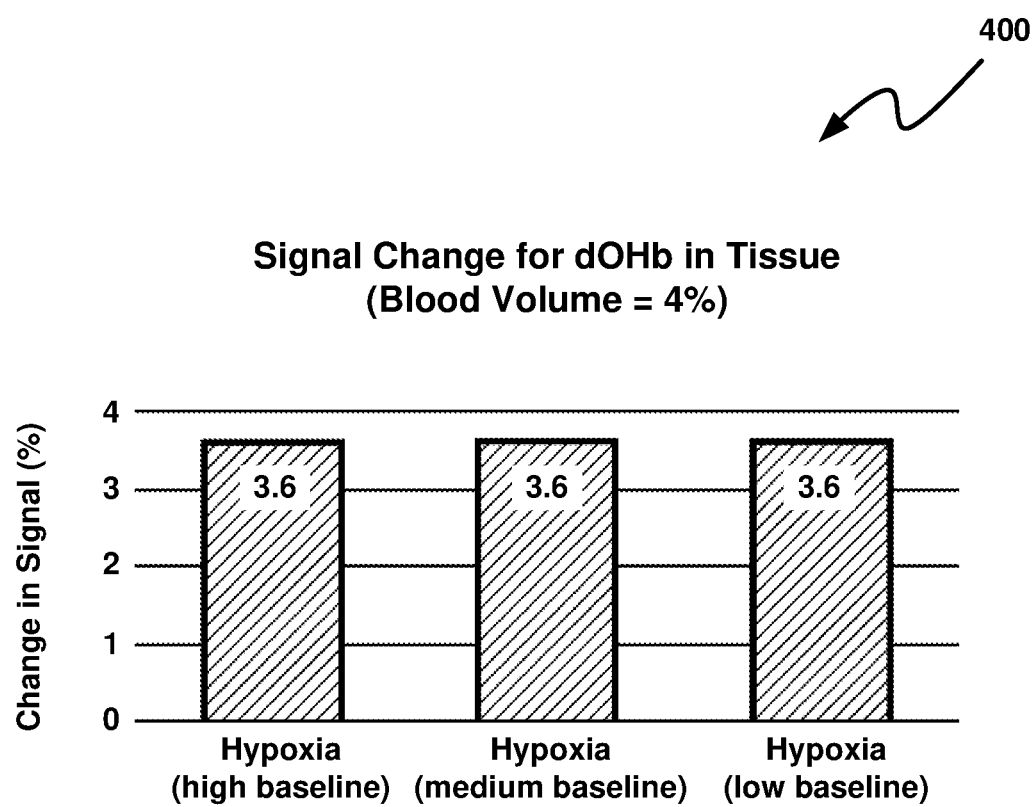
FIG. 4 is a graph showing the signal change in a tissue voxel during exemplary performance of the method of FIG. 2.
Figure 5:
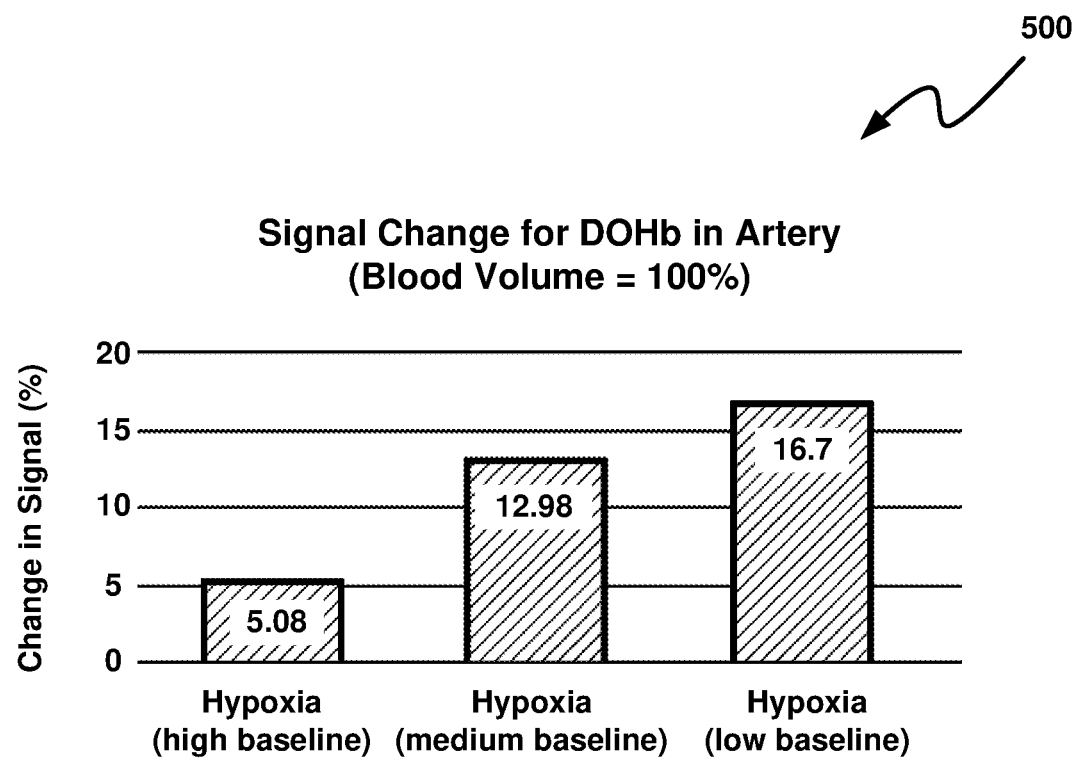
FIG. 5 is a graph showing the signal change in an arterial voxel during exemplary performance of the method of FIG. 2.
Figure 6:
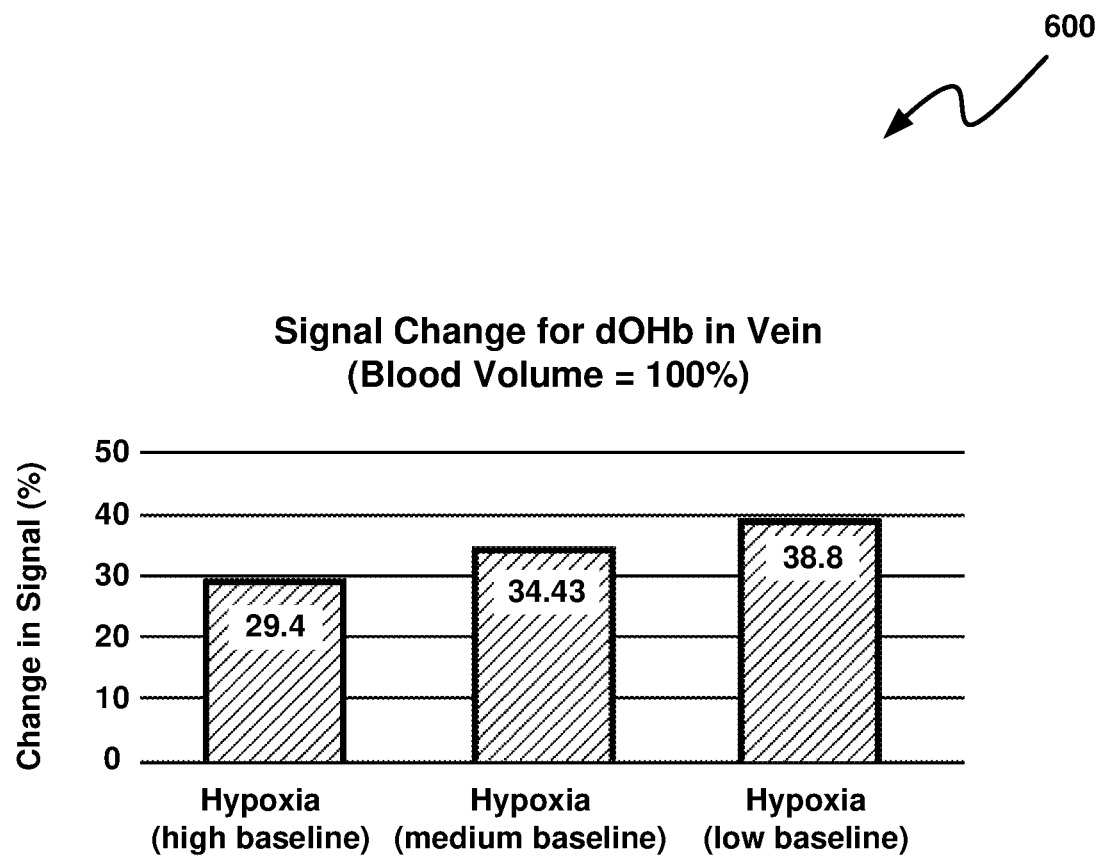
FIG. 6 is a graph showing the signal change in a venous voxel during exemplary performance of the method of FIG. 2.

Exemplary performance of method 200 is shown in FIGS. 4 to 6.

FIG. 4 shows a graph of the change in magnetic signal (%) for a voxel that is predominantly extravascular. The change in magnetic signal is approximately the same when the hypoxic bolus is implemented from a high baseline $P_aO_2$, a medium baseline $P_aO_2$, and a low baseline $P_aO_2$. Specifically, the change in magnetic signal is 3.6 for a high baseline $P_aO_2$, 3.6 for a medium baseline $P_aO_2$, and 3.6 for a low baseline $P_aO_2$. In this example, subtracting the ΔSI for the high baseline from ΔSI for the medium baseline would result in a difference of 0. Dividing the ΔSI for the medium baseline by the ΔSI for the high baseline would result in a dividend of 1. Therefore, the processor 126 would classify the voxel as extravascular. Because the blood volume in the voxel is so low, the baseline $P_aO_2$ has a negligible effect on the change in magnetic signal.

FIG. 5 shows a graph of the change in magnetic signal (%) for a voxel that is predominantly intravascular, and specifically contains a large artery. The change in magnetic signal is significantly higher when the hypoxic bolus is implemented from a medium baseline $P_aO_2$ as compared to a high baseline $P_aO_2$, and the change in magnetic signal is even higher when the hypoxic bolus is implemented from a low baseline $P_aO_2$. Specifically, the change in magnetic signal is 5.08 for a high baseline $P_aO_2$, 12.98 for a medium baseline $P_aO_2$, and 16.7 for a low baseline $P_aO_2$. In this example, subtracting the ΔBOLD for the high baseline from ΔBOLD for the medium baseline would result in a difference of 7.9. Since the difference is significantly higher than 0, the processor 126 would classify the voxel as intravascular. Dividing the ΔBOLD for the medium baseline by the ΔBOLD for the high baseline would result in a dividend of 2.56. Since the dividend is greater than 2, the processor 126 would classify the voxel as an artery. Because the blood volume in the voxel is so high, the baseline $P_aO_2$ has a significant effect on the change in magnetic signal.

FIG. 6 shows a graph of the change in magnetic signal (%) for a voxel that is predominantly intravascular, and specifically contains a large vein. The change in magnetic signal is significantly higher when the hypoxic bolus is implemented from a medium baseline $P_aO_2$ as compared to a high baseline $P_aO_2$, and the change in magnetic signal is even higher when the hypoxic bolus is implemented from a low baseline $P_aO_2$. Specifically, the change in magnetic signal is 29.4 for a high baseline $P_aO_2$, 34.43 for a medium baseline $P_aO_2$, and 38.8 for a low baseline $P_aO_2$. In this example, subtracting the ΔSI for the high baseline from ΔSI for the medium baseline would result in a difference of 5.03. Since the difference is significantly higher than 0, the processor 126 would classify the voxel as intravascular. Dividing the ΔSI for the medium baseline by the ΔSI for the high baseline would result in a dividend of 1.17. Since the dividend is greater than about 1 but less than 2, the processor 126 would classify the voxel as containing a vein. Because the extraction fraction of the arterial blood is reduced during hypoxia, the magnetic signal in the vein changes only slightly when the baseline is varied.

In some embodiments, instead of calculating ΔSI and basing the determination on a comparison between the first and second ΔSI, the processor 126 calculates the maximum relaxation rate and bases the determination on a comparison between the first and second maximum relaxation rates. The maximum relaxation rate for a voxel may be calculated according to Equation 2, where TE represents echo time and $\Delta R^*_{2,max}$ represents maximum relaxation time.

$$\Delta R^*_{2,max} = -\left(\frac{1}{TE}\right) * \ln\left(\frac{BOLD_{peak}}{BOLD_{baseline}}\right) \quad \text{Equation 2}$$

Echo time (TE) is the response time between the stimulus and the measure of the signal decay. TE may be calculated by the processor 126. Relaxation time represents the rate of signal decay or loss of synchronization from the radio wave frequency (RF) stimulus, which provides a measure of the dissipation of signal strength.

Figure 7:
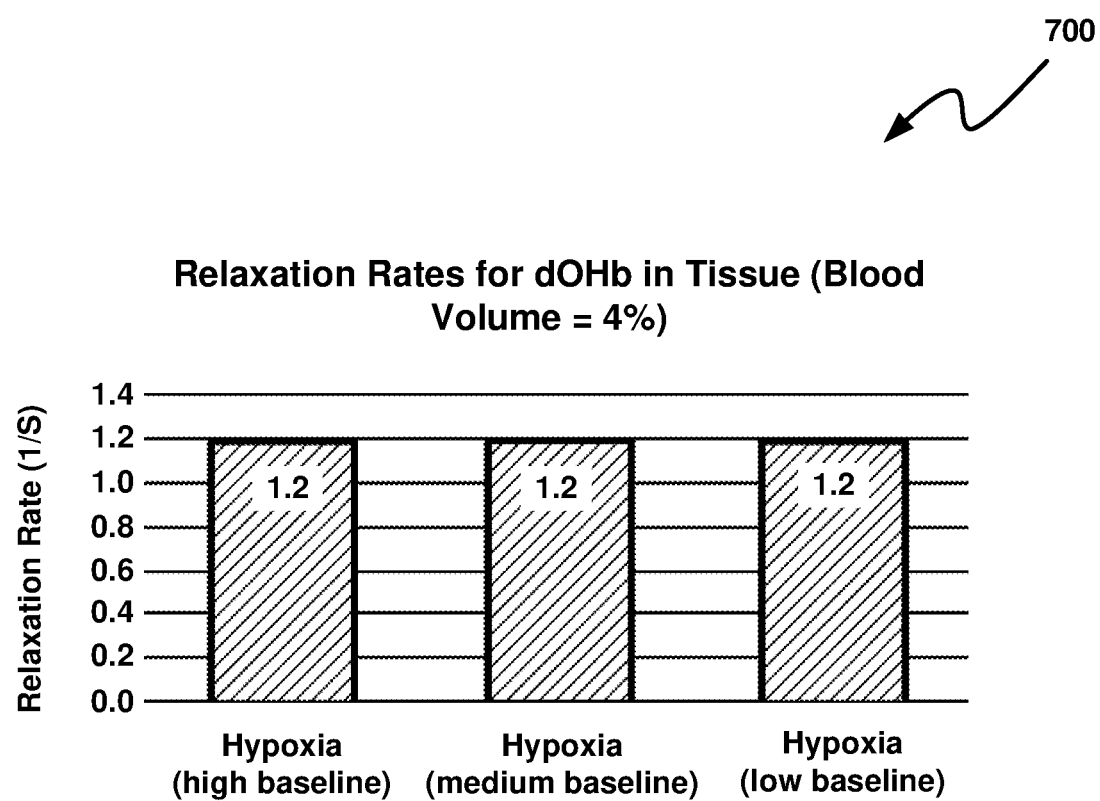
FIG. 7 is a graph showing the relaxation rate in a tissue voxel during exemplary performance of the method of FIG. 2.
Figure 8:
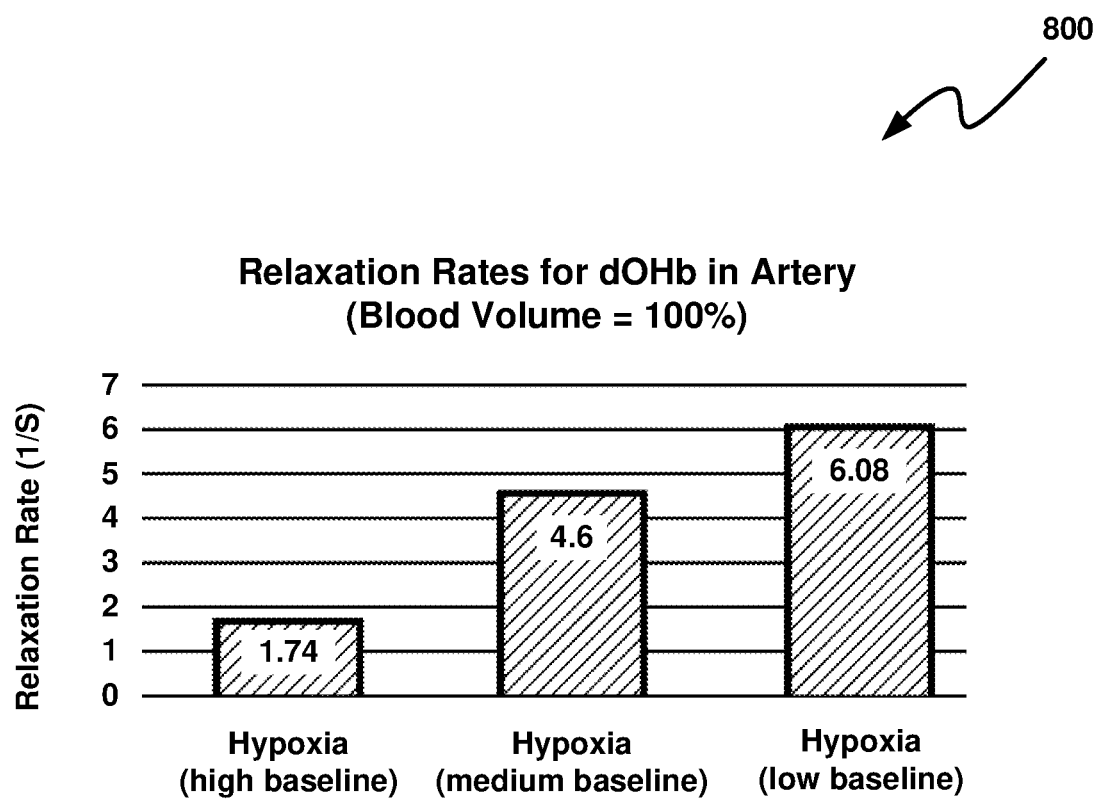
FIG. 8 is a graph showing the relaxation rate in an arterial voxel during exemplary performance of the method of FIG. 2.
Figure 9:
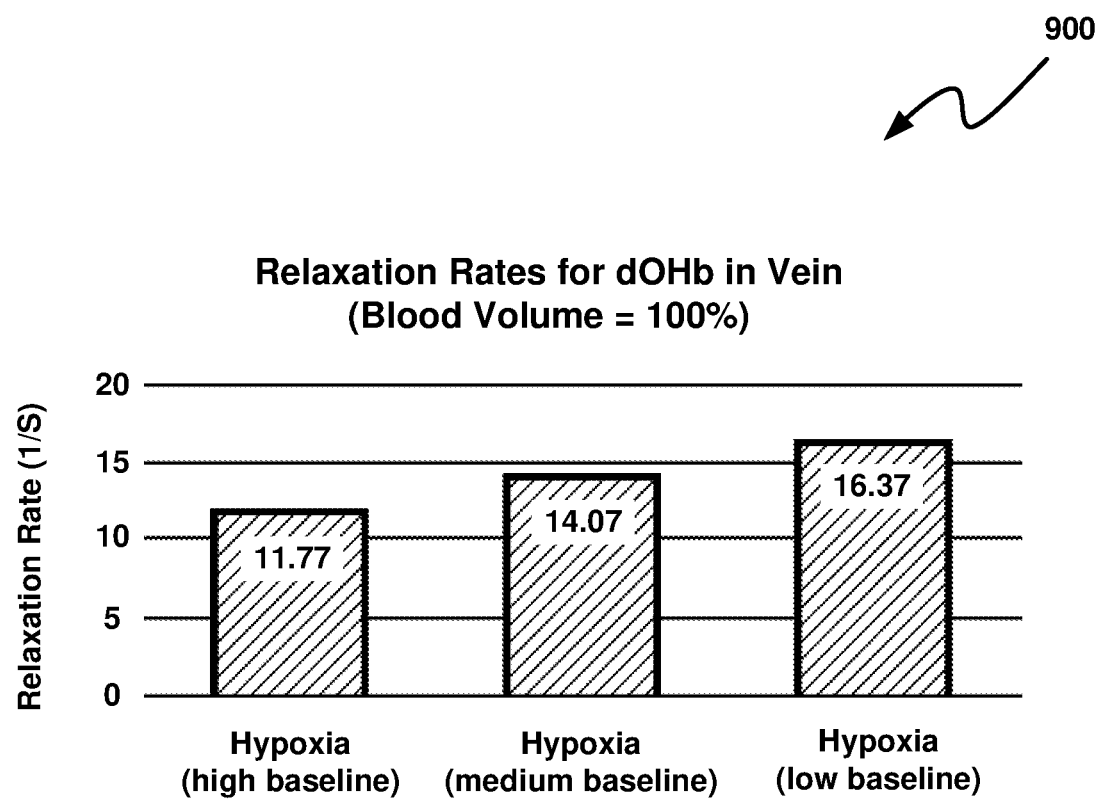
FIG. 9 is a graph showing the relaxation rate in a venous voxel during exemplary performance of the method of FIG. 2.

An example implementation of the method is shown in FIGS. 7 to 9.

FIG. 7 shows the relaxation rate (1/s) for a voxel that is predominantly extravascular. The relaxation rate is approximately the same when the hypoxic bolus is implemented from a high baseline $P_aO_2$, a medium baseline $P_aO_2$, and a low baseline $P_aO_2$. Specifically, the relaxation rate is 1.2 for a high baseline $P_aO_2$, 1.2 for a medium baseline $P_aO_2$, and 1.2 for a low baseline $P_aO_2$. In this example, subtracting the relaxation rate for the high baseline from relaxation rate for the medium baseline would result in a difference of 0. Dividing the relaxation rate for the medium baseline by the relaxation rate for the high baseline would result in a dividend of 1. Therefore, the processor 126 would classify the voxel as extravascular. Because the blood volume in the voxel is so low, the baseline $P_aO_2$ has a negligible effect on the relaxation rate.

FIG. 8 shows a graph of the relaxation rate for a voxel that is predominantly intravascular, and specifically contains a large artery. The relaxation rate is significantly higher when the hypoxic bolus is implemented from a medium baseline $P_aO_2$ as compared to a high baseline $P_aO_2$, and the relaxation rate is even higher when the hypoxic bolus is implemented from a low baseline $P_aO_2$. Specifically, the relaxation rate is 1.74 for a high baseline $P_aO_2$, 4.6 for a medium baseline $P_aO_2$, and 6.08 for a low baseline $P_aO_2$. In this example, subtracting the relaxation rate for the high baseline from relaxation rate for the medium baseline would result in a difference of 2.86. Since the difference is significantly higher than 0, the processor 126 would classify the voxel as intravascular. Dividing the relaxation rate for the medium baseline by the relaxation rate for the high baseline would result in a dividend of 2.64. Since the dividend is greater than 2, the processor 126 would classify the voxel as an artery. Because the blood volume in the voxel is so high, the baseline $P_aO_2$ has a significant effect on the relaxation rate.

FIG. 9 shows a graph of the relaxation rate for a voxel that is predominantly intravascular, and specifically contains a large vein. The relaxation rate is significantly higher when the hypoxic bolus is implemented from a medium baseline $P_aO_2$ as compared to a high baseline $P_aO_2$, and the change in magnetic signal is even higher when the hypoxic bolus is implemented from a low baseline $P_aO_2$. Specifically, the relaxation rate is 11.77 for a high baseline $P_aO_2$, 14.07 for a medium baseline $P_aO_2$, and 16.37 for a low baseline $P_aO_2$. In this example, subtracting the relaxation rate for the high baseline from relaxation rate for the medium baseline would result in a difference of 2.3. Since the difference is significantly higher than 0, the processor 126 would classify the voxel as intravascular. Dividing the relaxation rate for the medium baseline by the relaxation rate for the high baseline would result in a dividend of 1.2. Since the dividend is greater than about 1 but less than 2, the processor 126 would classify the voxel as containing a vein. Because the extraction fraction of the arterial blood is reduced during hypoxia, the relaxation rate in the vein changes only slightly when the baseline is varied.

The processor 126 may be further configured to repeat method 200 for a plurality of voxels. In some examples, the processor 126 may generate a brain map of the subject's brain or a portion of the subject's brain, the brain map indicating the location of arteries, veins, and cerebral tissue, based on the determinations made in method 200.

In the examples described above, the processor 126 classifies a voxel as vein, artery, or tissue, however the method 200 is not particularly limited. In other examples, the processor 126 assigns each voxel a score indicating the likelihood that it contains a vein, an artery, or tissue. In other examples, the processor 126 assigns each voxel a score indicating the relative blood volume in said voxel. The score is based on the dividend or difference calculated at block 220. The processor 126 may control the user interface 124 to display the score for one or a plurality of voxels. In further examples, the score may correspond to colour gradient and the processor 126 may generate a brain map displaying the scores for a plurality of voxels as colours. The brain map may be displayed at the user interface 124.

Figure 10:
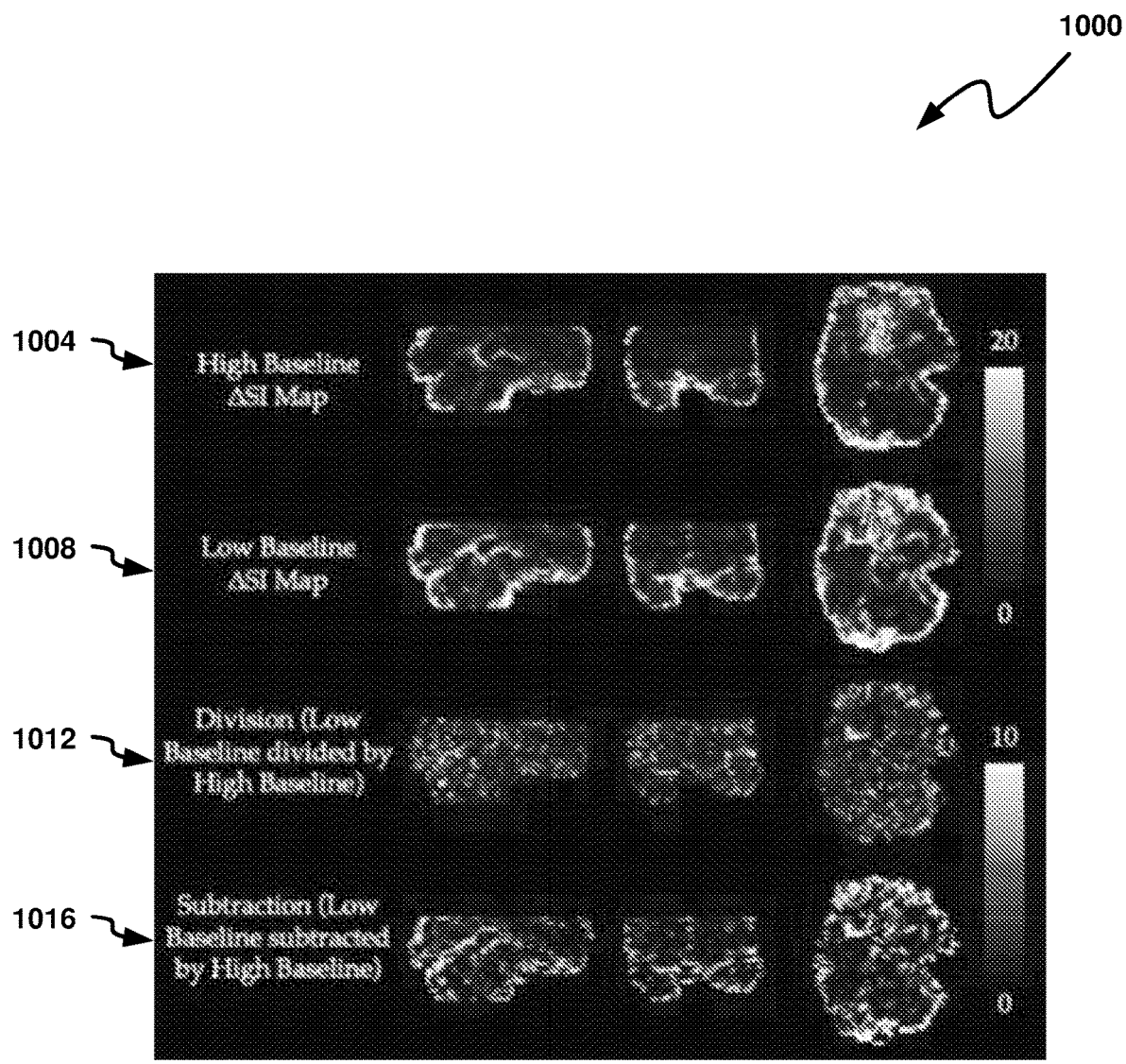
FIG. 10 is a set of brain maps obtained during exemplary performance of the method of FIG. 2.

FIG. 10 shows a set of brain maps obtained during exemplary performance of method 200. The calculated value for each voxel is represented by the brightness of the voxel as it is shown in the image. For the first two rows, a scale from 0 to 20 is shown on the top right. For the second two rows, a scale from 0 to 10 is shown on the bottom right. In row 1004, brain maps show the $\Delta SI$ value measured by the sensor 118 when the SGD device 101 implements a hypoxic bolus from a high baseline $P_aO_2$. In the second row 1008, brain maps show the $\Delta SI$ value measured by the sensor 118 when the SGD device 101 implements a hypoxic bolus from a low baseline $P_aO_2$. In the third row 1012, brain maps show the dividend calculated by dividing the $\Delta SI$ value obtained from a low baseline $P_aO_2$ by the $\Delta SI$ value obtained from a high baseline $P_aO_2$. In row 1016, brain maps show the difference between the $\Delta SI$ value obtained from a low baseline $P_aO_2$ and the $\Delta SI$ value obtained from a high baseline $P_aO_2$.

Figure 11:
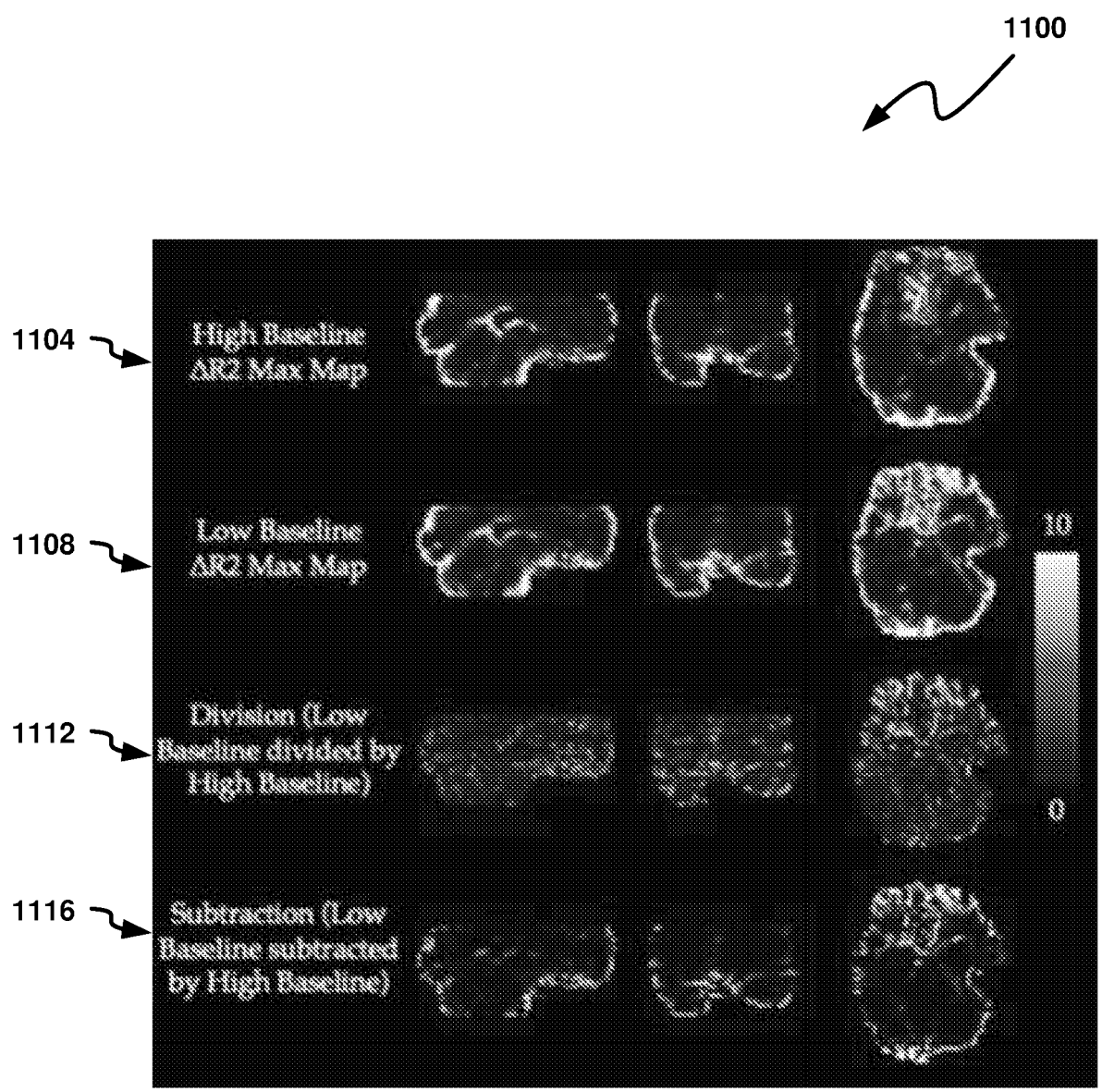
FIG. 11 is another set of brain maps obtained during exemplary performance of the method of FIG. 2.

FIG. 11 shows another set of brain maps obtained during exemplary performance of method 200. The calculated value for each voxel is represented by the brightness of the voxel as it is shown in the image. A scale from 0 to 10 is shown on the right. In the first row 1104, brain maps show In the first row 1104, brain maps show the $\Delta R^*_{2,max}$ calculated by the processor 126 when the SGD device 101 implemented a hypoxic bolus from a high baseline $P_aO_2$. In row 1108, brain maps show the $\Delta R_{2,max}$ calculated by the processor 126 when the SGD device 101 implemented a hypoxic bolus from a low baseline $P_aO_2$. In row 1112, brain maps show the dividend calculated by dividing the $\Delta R^*_{2,max}$ obtained from a low baseline $P_aO_2$ by the $\Delta R^*_{2,max}$ obtained from a high baseline $P_aO_2$. In row 1116, brain maps show the difference calculated by subtracting the $R^*_{2,max}$ obtained from a low baseline $P_aO_2$ and the $\Delta R^*_{2,max}$ obtained from a high baseline $P_aO_2$.

Comparing row 1104 to row 1108 shows that higher $\Delta R^*_{2max}$ values are obtained from a lower baseline $P_aO_2$, but it is not clear where the vessels are located. Comparing row 1112 to row 1108 reveals the location of arteries. Areas that are brighter in row 1112 than in row 1108 indicate the presence of arteries. When comparing row 1016 to row 1112, it can be seen that extravascular voxels are dark in row 1112 and the only light areas indicate major arteries. In particular, the middle cerebral artery is prominent when comparing the axial slice in row 1116 to the axial slice in row 1112.

The present disclosure provides a new method for differentially highlighting the properties of venous and arterial voxels. By generating two deoxyhemoglobin boluses with the same hypoxic drop but distinct baseline oxygenations, arteries and veins can be distinguished. The bolus with the lower baseline oxygenation increases the signal of arterial and venous voxels while keeping tissue signal relatively unchanged. The signal changes for both venous and arterial voxels increase with a drop in baseline oxygenation, however the arterial signal change is much larger. Thus, the subtraction method allows high blood volume vasculature to be highlighted while the division method allows veins to be differentiated from arteries.

A further benefit of the disclosed method is that it is non-invasive and causes few adverse reactions. Because deoxyhemoglobin is an endogenous molecule that does not accumulate or recirculate, it is safe and possible to administer multiple boluses of the contrast agent. Repeated changes in [dOHb] are well-tolerated by individuals and therefore individuals and populations can be studied over time.

The many features and advantages of the invention are apparent from the detailed specification and, thus, it is intended by the appended claims to cover all such features and advantages of the invention that fall within the true spirit and scope of the invention. Further, since numerous modifications and changes will readily occur to those skilled in the art, it is not desired to limit the invention to the exact construction and operation illustrated and described, and accordingly all suitable modifications and equivalents may be resorted to, falling within the scope of the invention.

What is claimed is:

1. A method of identifying the vascularity of cerebral tissue in a subject, the method comprising:
   inducing a first change in partial pressure of oxygen in arterial blood ($\Delta P_aO_2$) in the subject using a sequential gas delivery device;
   wherein inducing the first change in partial pressure of oxygen in arterial blood ($\Delta PaO_2$) comprises targeting a first baseline partial pressure of oxygen in arterial blood ($PaO_2$) in the subject and subsequently targeting a first signal partial pressure of oxygen in arterial blood ($PaO_2$) in the subject; and
   wherein the first signal partial pressure of oxygen in arterial blood ($PaO_2$) is lower than the first baseline partial pressure of oxygen in arterial blood ($PaO_2$);
   determining a first change in magnetic signal ($\Delta SI$) in a voxel of the subject's brain using a magnetic resonance imaging device while inducing the first change partial pressure of oxygen in arterial blood ($\Delta PaO_2$);
   inducing a second change in partial pressure of oxygen in arterial blood ($\Delta PaO_2$) in the subject using the sequential gas delivery device;
   wherein inducing the second change in partial pressure of oxygen in arterial blood ($\Delta PaO_2$) comprises targeting a second baseline partial pressure of oxygen in arterial blood ($PaO_2$) in the subject and subsequently targeting a second signal partial pressure of oxygen in arterial blood ($PaO_2$) in the subject; and
   wherein the second signal partial pressure of oxygen in arterial blood ($PaO_2$) is lower than the second baseline partial pressure of oxygen in arterial blood ($PaO_2$); and
   wherein the second baseline partial pressure of oxygen in arterial blood ($PaO_2$) is lower than the first baseline partial pressure of oxygen in arterial blood ($PaO_2$);
   determining a second change in magnetic signal ($\Delta SI$) in the voxel of the subject's brain using the magnetic resonance imaging device while inducing the second change partial pressure of oxygen in arterial blood ($\Delta PaO_2$);
   comparing the first and second changes in magnetic signal ($\Delta SI$); and
   based on the comparison, outputting a signal at a user interface connected to the magnetic resonance imaging device, the signal indicating whether the voxel is extravascular or intravascular.

2. The method of claim 1 wherein the first change in partial pressure of oxygen in arterial blood ($\Delta PaO_2$) is approximately equal to the second change in partial pressure of oxygen in arterial blood ($\Delta PaO_2$).

3. The method of claim 2 wherein comparing the first and second changes in magnetic signal ($\Delta SI$) comprises calculating a difference between the first and second changes in magnetic signal ($\Delta SI$), the method further comprising:
- if the first change in magnetic signal ($\Delta SI$) is approximately equal to the second change in magnetic signal ($\Delta SI$), outputting a signal at the user interface indicating that the voxel is extravascular; and
- if the second change in magnetic signal ($\Delta SI$) is higher than the first change in magnetic signal ($\Delta SI$), outputting a signal at the user interface indicating that the voxel is intravascular.

4. The method of claim 2 wherein comparing the first and second changes in magnetic signal ($\Delta SI$) comprises dividing the second change in magnetic signal ($\Delta SI$) by the first change in magnetic signal ($\Delta SI$) to obtain a dividend, the method further comprising:
- if the dividend is approximately 1, outputting a signal at the user interface indicating that the voxel is extravascular; and
- if the dividend is greater than approximately 1, outputting a signal at the user interface indicating that the voxel is intravascular.

5. The method of claim 4 further comprising:
comparing the dividend to a pre-determined threshold,
- if the dividend is less than or equal to the pre-determined threshold, outputting a signal at the user interface indicating that the voxel contains a vein; and
- if the dividend is greater than the pre-determined threshold, outputting a signal at the user interface indicating that the voxel contains an artery.

6. The method of claim 1 further comprising maintaining normocapnia while inducing the first and second changes in partial pressure of oxygen in arterial blood ($\Delta PaO_2$).

7. The method of claim 2 wherein the first baseline partial pressure of oxygen in arterial blood ($PaO_2$) is between 85 and 100 mmHg.

8. The method of claim 2 wherein the second baseline partial pressure of oxygen in arterial blood ($PaO_2$) is between 75 and 85 mmHg.

9. A non-transitory machine-readable medium comprising instructions that, when executed by a processor, cause the processor to perform the method of claim 1.

10. An apparatus for identifying the vascularity of cerebral tissue in a subject, the apparatus comprising:
- a sequential gas delivery device configured to control the partial pressure of oxygen in arterial blood in the subject;
- a processor connected to the sequential gas delivery device and configured to control the sequential gas delivery device to induce a first and second change in partial pressure of oxygen in arterial blood ($\Delta PaO_2$) in the subject;
  - wherein inducing the first change in partial pressure of oxygen in arterial blood ($\Delta PaO_2$) comprises targeting a first baseline partial pressure of oxygen in arterial blood ($PaO_2$) in the subject and subsequently targeting a first signal partial pressure of oxygen in arterial blood ($PaO_2$) in the subject;
  - wherein the first signal partial pressure of oxygen in arterial blood ($PaO_2$) is lower than the first baseline partial pressure of oxygen in arterial blood ($PaO_2$);
  - wherein inducing the second change in partial pressure of oxygen in arterial blood ($\Delta PaO_2$) comprises targeting a second baseline partial pressure of oxygen in arterial blood ($PaO_2$) in the subject and subsequently targeting a second signal partial pressure of oxygen in arterial blood ($PaO_2$) in the subject;
  - wherein the second signal partial pressure of oxygen in arterial blood ($PaO_2$) is lower than the second baseline partial pressure of oxygen in arterial blood ($PaO_2$); and
  - wherein the second baseline partial pressure of oxygen in arterial blood ($PaO_2$) is lower than the first baseline partial pressure of oxygen in arterial blood ($PaO_2$);
- a sensor connected to the processor and configured to:
  - determine a first change in magnetic signal ($\Delta SI$) in a voxel of the subject's brain while the sequential gas delivery device induces the first change partial pressure of oxygen in arterial blood ($\Delta PaO_2$); and
  - determine a second change in magnetic signal ($\Delta SI$) in the voxel of the subject's brain while the sequential gas delivery device induces the second change partial pressure of oxygen in arterial blood ($\Delta PaO_2$);
  - wherein the processor is further configured to receive the first and second changes in magnetic signal ($\Delta SI$) from the sensor and compare the first and second changes in magnetic signal ($\Delta SI$); and
- a user interface connected to the processor, the user interface configured to output a signal indicating whether the voxel is extravascular or intravascular, based on the comparison.

11. The apparatus of claim 10 wherein the user interface is further configured to output a signal indicating whether the voxel contains an artery or a vein, based on the comparison.

* * * * *